United States Patent
Dötterl et al.

(10) Patent No.: US 8,487,153 B2
(45) Date of Patent: Jul. 16, 2013

(54) SELECTIVE OLEFIN DIMERIZATION WITH SUPPORTED METAL COMPLEXES ACTIVATED BY ALKYLALUMINUM COMPOUNDS OR IONIC LIQUIDS

(75) Inventors: Matthias Dötterl, Bayreuth (DE);
Roland Schmidt, Bartlesville, OK (US);
Tanja Englmann, Immenreuth (DE);
Christine Denner, Gefrees (DE);
Helmut G. Alt, Bayreuth (DE)

(73) Assignee: Phillips 66 Company, Houston, TX (US)

( * ) Notice: Subject to any disclaimer, the term of this patent is extended or adjusted under 35 U.S.C. 154(b) by 352 days.

(21) Appl. No.: 12/828,797

(22) Filed: Jul. 1, 2010

(65) Prior Publication Data

US 2011/0004039 A1    Jan. 6, 2011

Related U.S. Application Data

(60) Provisional application No. 61/222,436, filed on Jul. 1, 2009.

(51) Int. Cl.
*C07C 2/22* (2006.01)

(52) U.S. Cl.
USPC .......... 585/513; 585/502; 585/510; 585/511; 585/520; 585/521; 585/522; 585/523

(58) Field of Classification Search
USPC ............... 585/502, 510, 511, 512, 513, 520, 585/521, 522, 523
See application file for complete search history.

(56) References Cited

U.S. PATENT DOCUMENTS

| 5,955,555 | A  | * | 9/1999 | Bennett | 526/133 |
| 6,291,733 | B1 | * | 9/2001 | Small et al. | 585/512 |

(Continued)

FOREIGN PATENT DOCUMENTS

WO    WO 9847616 A1 * 10/1998

OTHER PUBLICATIONS

Gates, "Catalysis" in Kirk-Othmer Encyclopedia of Chemical Technology, 2002, John Wiley & Sons, available on-line Aug. 16, 2002.*

(Continued)

*Primary Examiner* — In Suk Bullock
*Assistant Examiner* — Bradley Etherton
(74) *Attorney, Agent, or Firm* — Teresa J. Lechner-Fish

(57) ABSTRACT

Methods for dimerizing alpha-olefins utilizing immobilized buffered catalysts wherein a buffered ionic liquid is mixed with an organometallic complex of the formula:

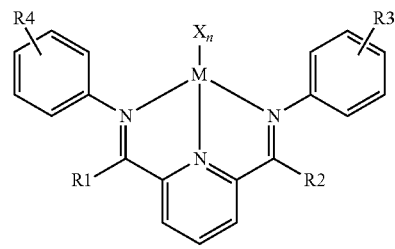

where X is a halogen, n=2 or 3, M=Ti, V, Cr, Mn, Fe, Co and Ni and R1, R2, R3 and R4 are selected from the group consisting of hydrogen, alkyl, aryl, alkenyl, alkynyl, alkyloxy, substituted aryl, and X are provided. A method for dimerizing alpha-olefins utilizing the immobilized buffered catalysts and a co-catalyst is also provided.

10 Claims, 1 Drawing Sheet

U.S. PATENT DOCUMENTS

| | | | |
|---|---|---|---|
| 6,458,905 B1* | 10/2002 | Schmidt et al. | 526/172 |
| 6,555,723 B2* | 4/2003 | Schiffino | 585/521 |
| 2001/0049331 A1 | 12/2001 | Chang | |
| 2002/0177744 A1* | 11/2002 | Small et al. | 585/16 |
| 2006/0014989 A1* | 1/2006 | De Boer et al. | 585/324 |
| 2007/0155621 A1* | 7/2007 | Lavastre et al. | 502/200 |

OTHER PUBLICATIONS

Mehnert, "Supported ionic Liquid Catalysts" in Chem. Eur. J., 2005, 11, 50-56—month unknown.*

Walas, "Chemical Reactors" in Perry's Chemical Engineer's Handbook, 7th ed., 1997, McGraw-Hill, available on-line at www.knovel.com.*

International Search Report and Written Opinion issued Sep. 1, 2010 for International Application PCT/US2010/040848.

Tellmann, et al. "Selective Dimerization/Oligomerization of r-Olefins by Cobalt Bis(imino)pyridine Catalysts Stabilized by Trifluoromethyl Substituents: Group 9 Metal Catalysts with Productivities Matching Those of Iron Systems" Organometallics, vol. 24, Issue 2, Jan. 17, 2005, pp. 280-286.

* cited by examiner

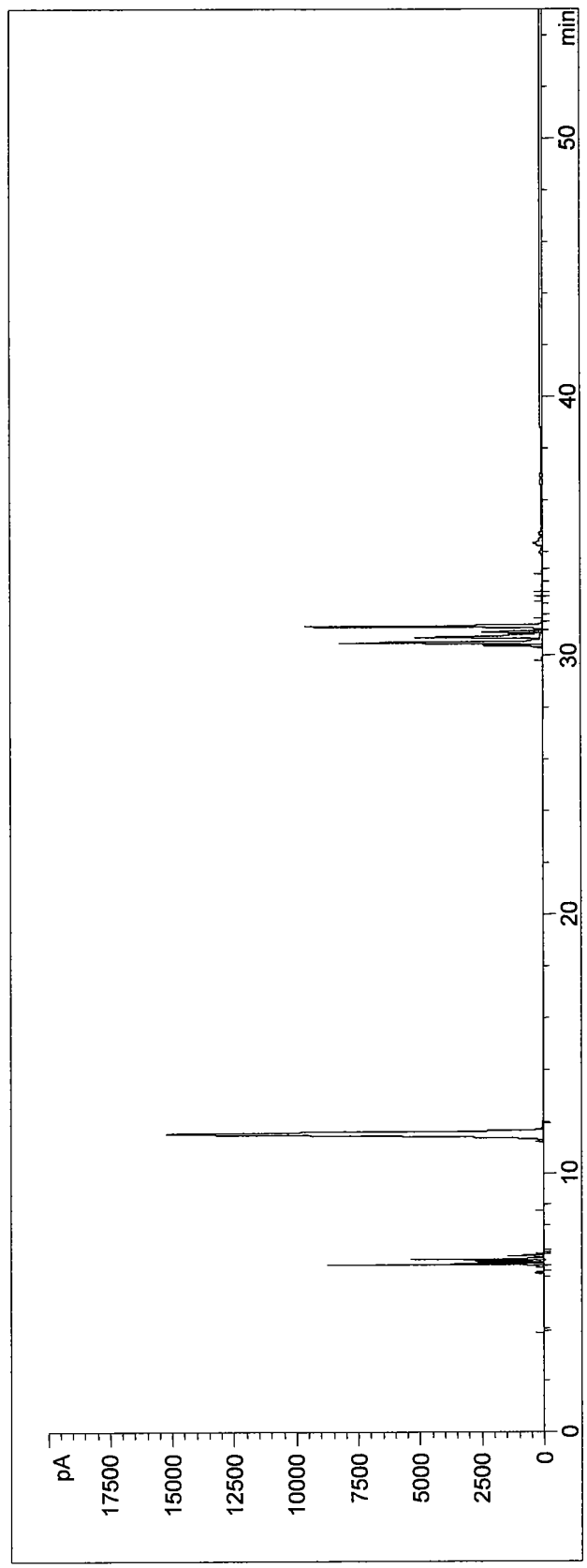

SELECTIVE OLEFIN DIMERIZATION WITH SUPPORTED METAL COMPLEXES ACTIVATED BY ALKYLALUMINUM COMPOUNDS OR IONIC LIQUIDS

CROSS REFERENCE TO RELATED APPLICATIONS

This application claims priority to U.S. Provisional Application No. 61/222,436, filed Jul. 1, 2009.

FEDERALLY SPONSORED RESEARCH STATEMENT

Not applicable.

REFERENCE TO MICROFICHE APPENDIX

Not applicable.

FIELD OF THE INVENTION

The invention relates to processes for dimerizing alkenes.

BACKGROUND OF THE INVENTION

Dimerization of olefins is well known and industrially useful. Further, the use of transition metals to catalyze olefin dimerization and oligomerization is also known.

Use of ionic liquids for dimerization and oligomerization of olefins is also well known. In the broad sense, the term ionic liquids includes all molten salts, for instance, sodium chloride at temperatures higher than 800° C. Today, however, the term "ionic liquid" is commonly used for salts whose melting point is relatively low (below about 100° C.). One of the earliest known room temperature ionic liquids was [EtNH$_3$]+[NO$_3$] (m.p. 12° C.), the synthesis of which was published in 1914. Much later, series of ionic liquids based on mixtures of 1,3-dialkylimidazolium or 1-alkylpyridinium halides and trihalogenoaluminates, initially developed for use as electrolytes, were to follow.

One property of the imidazolium halogenoaluminate salts was that they were tuneable, i.e., viscosity, melting point and the acidity of the melt could be adjusted by changing the alkyl substituents and the ratio of imidazolium or pyridinium halide to halogenoaluminate. Imidazolium halogenoaluminate salts exhibit moisture sensitivity and, depending on the ratio of aluminum halide, Lewis acidic or Lewis basic properties. Ionic liquids with 'neutral', weakly coordinating anions such as hexafluorophosphate ([PF$_6$]$^-$) and tetrafluoroborate ([BF$_4$]$^-$) have also been used as alternatives to imidazolium halogenoaluminate salts. [PF$_6$]$^-$ and [BF$_4$]$^-$ based ionic liquids are generally highly toxic. Yet another anion for use in ionic liquids is bistriflimide [(CF$_3$SO$_2$)$_2$N]$^-$, which does not exhibit the toxicity of [PF$_6$]$^-$ and [BF$_4$]$^-$ anions. Ionic liquids with less toxic cations are also known, including those with compounds like ammonium salts (such as choline) being used in lieu of imidazole.

Ionic liquids have found use as a catalyst in various chemical reactions. For example, Lewis acidic ionic liquids have been used as a catalyst to alkylate aromatic hydrocarbons, such as the alkylation of benzene with ethylene. In such processes, the ionic liquid itself serves as the catalyst, and the catalyst is neither buffered nor immobilized on a support. Ionic liquids have also been used in processes for making high viscosity polyalphaolefins using an oligomerization catalyst including an aluminum halide or alky-aluminum halides, and alkyl-substituted imidazolium halide or pyridinium halide. In such processes, the ionic liquid itself again serves as the catalyst and preferentially forms high-viscosity polyalphaolefins due to the lack of buffering.

Processes utilizing immobilized ionic liquids are also known. For example, immobilized ionic liquids may be prepared by functionalizing a support prior to contact with or forming the ionic liquid. Such known immobilized ionic liquids however are not buffered and therefore preferentially form high viscosity polyolefins. Again, in such systems, the ionic liquid itself functions as the catalyst.

Although all of the above methods are known and used in the synthesis of olefins, what is needed in the art is an improved synthetic method that allows for easy separation of the product. Especially in the case of olefin dimerizations, which usually yield liquids with relatively low viscosities or even gaseous olefins, the application of supported systems that allows the use of fixed bed reactors is superior to batch oligomerization, obviating the need for further product separation. In addition, the catalytically active surface may be maximized by use of high surface support materials, which optimizes the catalytic performance.

SUMMARY OF THE INVENTION

Some embodiments of the invention provide a process for the dimerization of olefins comprising the steps of: modifying a support material containing —OH groups with an alkylaluminum compound to form a modified support material; mixing an ionic liquid having a melting point below about 100° C. with an organometallic complex of the formula:

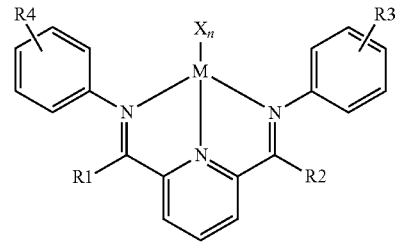

where X is a halogen, n=2 or 3, M=Ti, V, Cr, Mn, Fe, Co and Ni and R1, R2, R3 and R4 are selected from the group consisting of hydrogen, alkyl, alkenyl, alkynyl, alkyloxy, substituted aryl, and X to form an ionic liquid/catalyst complex; mixing the ionic liquid/catalyst complex with the modified support material to form an immobilized buffered catalyst; and mixing the immobilized buffered catalyst with one or more alpha-olefins.

In some embodiments, M=Fe, X=Cl, n=3 and R1, R2, R3 and R4=H. In yet other embodiments, the one or more alpha-olefins is selected from the group alkenes having between three and ten carbon atoms.

In certain embodiments of the invention, the ionic liquid comprises a salt selected from the group consisting of AlCl$_3$, AlRCl$_2$ and AlR$_2$Cl, where R is an alkyl chain. In yet other embodiments of the invention, the ionic liquid comprises a cation selected from the group consisting of ammonium, imidazolium, sulfonium and phosphonium salts. In a particular embodiment, the alkylaluminum compound is chlororthylaluminum.

Other embodiments of the invention provide a process for the dimerization of olefins comprising the steps of: modifying a support material containing —OH groups with an alkylaluminum compound to form a modified support material; mixing an organometallic complex of the formula:

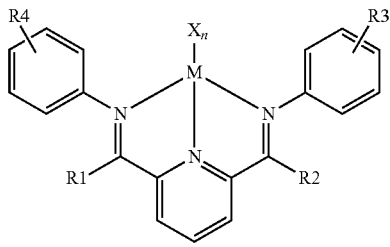

where X is a halogen, n=2 or 3, M=Ti, V, Cr, Mn, Fe, Co and Ni and R1, R2, R3 and R4 are selected from the group consisting of hydrogen, alkyl, aryl, alkenyl, alkynyl, alkloxy, substituted aryl, and X with one or more co-catalysts selected from the group of methylaluminoxane (MAO) and $B(C_6F_5)_3$ to form a combined catalyst; mixing the combined catalyst with one or more alpha-olefins.

BRIEF DESCRIPTION OF THE DRAWINGS

FIG. 1 is a gas chromatographic spectra of the reaction products produced after five hours reaction per Example 2.

DESCRIPTION OF EMBODIMENTS OF THE INVENTION

In one embodiment of the invention, a process for dimerizing olefins utilizes an organometallic catalyst dissolved in a buffered ionic liquid immobilized on a support material.

For example, support material containing —OH groups may be modified with one or more aluminumhalide, alkylaluminumdihalide, and dialkylaluminumhalide or trialkylaluminum compounds (generically, "$AlX_nR_{3-n}$"). Generally, to achieve the support modification, the support material is mixed with a solution of the $AlX_nR_{3-n}$, with stirring. Suitable solvents include aromatics and paraffins having 5 or more carbon atoms, including by way of example, toluene, benzene, pentane, hexane, cyclohexane and dichloromethane.

Excess solvent may be removed following a reaction time from between about 2 minutes to about 30 minutes, preferably between about 5 and 25 minutes and most preferably between about 10 and about 20 minutes. The result is a coated support material. Equation (1) below illustrates an exemplary formation of a modified support according to one embodiment of the invention.

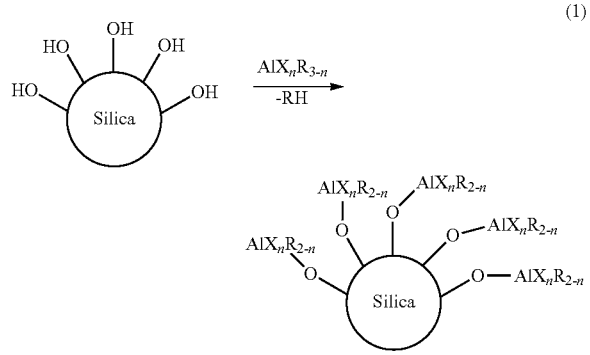

(1)

The ionic liquid is primarily a salt or mixture of salts that melt below room temperature. In some embodiments of the invention, the ionic liquid salt may be one or more of aluminum halide, alkylaluminum halide, gallium halide or alkylgallium halide. Preferably, the ionic liquid salt is one or more of $AlCl_3$, $AlRCl_2$, or $AlR_2Cl$ where R is an alkyl chain. In some embodiments of the invention, the ionic liquid cation may be ammonium, imidazolium, sulfonium or phosphonium salt. In preferred embodiments, the ionic liquid cation is selected from ammonium halides containing one or more alkyl moieties having from 1 to about 9 carbon atoms, such as, for example, triethylmethylbenzylammoniumchloride, or hydrocarbyl substituted imidazolium halides, such as, for example, 1-butyl-3-methylimidazolium chloride.

The ionic liquid which will be used in producing the novel catalyst composition may be produced by first separately dissolving each of an acceptable cation and an acceptable anion in a solvent. The dissolved cation and anion are then mixed followed by removal of solvent.

In some embodiments of the invention, the ionic liquid is buffered. For example, a buffered system of ionic liquid may be produced utilizing one or more buffers having the general formula $R_4Al_2Cl_2$ or $R_2Al_2Cl_4$ where the neutral compounds are dissolved in an organic phase. For example:

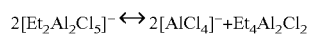

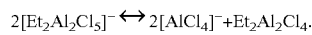

In some embodiments, the quarternary amine is dissolved first in methylene chloride and $AlCl_3$ and stirred between 1 and 20 hours. The solvent is then removed by any of a number of known methods, most preferably by vacuum. The buffered system is then formed by addition of about 0.001 to about 0.2 equivalents $Et_2AlCl$ to yield a ratio of the buffered system of amine: $AlCl_3$:$Et_2AlCl$ of about 1:1.22:0.2.

An organometallic catalyst is then mixed with the ionic liquid. The organometallic catalyst may be selected from the group of halogenated organometallic complexes wherein the metal is selected from the group consisting of Ti, V, Cr, Mn, Fe, Co and Ni and having the general formula shown by the formula below:

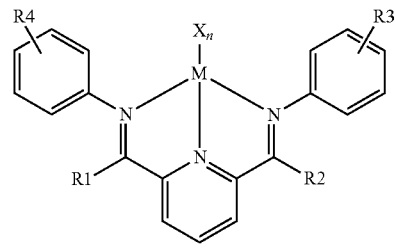

where X is a halogen, n=2 or 3, M=Ti, V, Cr, Mn, Fe, Co and Ni and R1, R2, R3 and R4 are selected from the group consisting of hydrogen, alkyl, aryl, alkenyl, alkynyl, alkyloxy, substituted aryl, and X.

The immobilized buffered catalyst is then formed by mixing the organometallic catalyst/ionic liquid composition with the coated support material. Following sufficient mixing, excess solvent is removed, leaving an immobilized buffered catalyst solid or powder material. The immobilized buffered catalyst may then be mixed with one or more alpha-olefins to dimerize the olefins. In some embodiments, the immobilized buffered catalyst is mixed with a single alpha-olefin to form homogenous dimers or oligomers having fifty or fewer monomer units.

Example 1

Silica Modification:

Commercially available silica (DAVICAT® SI 1102 from W.R. GRACE & CO®) was calcined at 400° C. in dry argon for 4 hours. The calcined silica (13.97 g) was slowly added to a 1 molar solution of $Et_2AlCl$ in toluene with vigorous stirring (45 ml, 3-3.5 ml per g of calcined silica) and further stirred for 10-20 minutes. The toluene solution was decanted and the silica washed 3 times with toluene.

Ionic Liquid Preparation:

20.89 g 1-butyl-3-methylimidazolium chloride ("[BMIM] Cl") 95%, BASF) was dissolved in $CH_2Cl_2$. 19.43 g $AlCl_3$ (1.22 mol. eq., REAGENT PLUS, SIGMA-ALDRICH™) was suspended in 100 ml $CH_2Cl_2$ and the suspension was slowly transferred to the solution of [BMIM]Cl. This addition was exothermic. The methylene chloride solvent was removed by subjecting the mixture to vacuum, heated to 70° C. and left on high vacuum until no more bubbles were observed. The result was a viscous, slightly colored liquid.

Catalyst Preparation:

10 ml of the ionic liquid was placed in a schlenk tube and 47.5 mg of unsubstituted bis(imino)pyridine-Fe(III)chloride-complex (0.01 mmol/ml) was added and the mixture stirred for a few seconds.

Catalyst Coating:

The toluene suspension of the coated support material was slowly added to 8.9 ml (80 wt %) of the catalyst containing ionic liquid with vigorous stirring. This mixture was stirred for 15 minutes to produce an immobilized buffered catalyst as shown in equation (2) below. The toluene solvent was then decanted and the remainder of the toluene was removed by application of high vacuum to produce a powder.

(2)

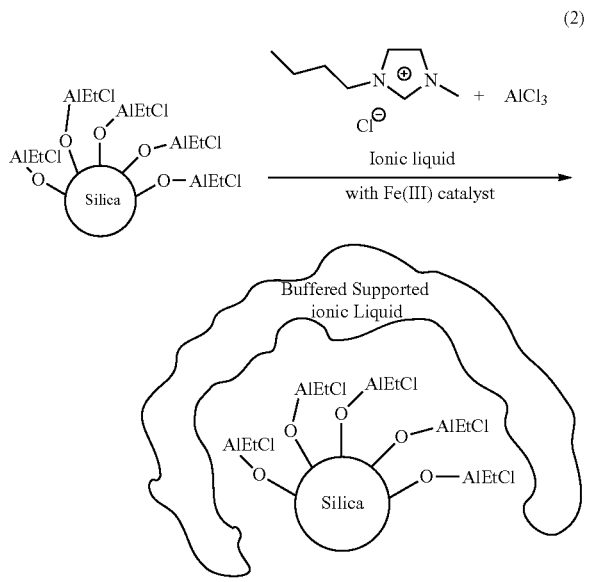

Dimerization of Propene in a Pressure Schlenk Tube:

2.92 g of the prepared supported buffered catalyst was placed in a pressure schlenk tube, vacuum applied and 50 ml of liquid propene (>99.3% purity) condensed into the tube using liquid nitrogen. The schlenk tube was then placed in a room temperature water bath and stirred for 90 minutes. After the pressure was released, 20.67 g of oligomer product remained in the schlenk tube, which equals about 1550 kg Oligomer/mol×h. Gas Chromatography ("GC") analysis revealed a dimer content of 95.9%.

Dimerization of Propene in a Fixed Bed Reactor:

The remainder of the immobilized buffered powder catalyst (26.30 g) was loaded into a reactor tube. The reactor was run with a flow rate of 1 ml/min, 40° C., 20 bar, 20 wt % propene in pentane feed. Six samples were taken, each containing 94-96% dimers. Two cooled samples (dry ice, acetone+isopropanol) were taken revealing conversions of about 58% after 6 hours and about 14% after 12 hours. The peak intensities of the fractions, which were taken without cooling, showing conversion at 3 hours, 4 hours and 5 hours, respectively, are not shown, but available on request.

In another embodiment of the invention, alpha olefins are homogenously dimerized using organometallic complexes with selected co-catalysts. Specifically, oganometallic complexes of the form shown above may be mixed with one or more co-catalysts selected from the group of methylaluminoxane (MAO) and $B(C_6F_5)_3$. The methylaluminoxane may be used in different ratios vis a vis the organometallic catalyst, ranging from about 100:1 to about 1000:1 co-catalyst:catalyst. Most preferably, MAO is used as a co-catalyst in a ratio between about 250:1 to about 750:1 co-catalyst:catalyst.

For the homogenous catalyzed reactions MAO, $AlCl_3$, $AlR_3$, $AlR_2Cl$, $AlBu/AlCl_3$, $AlR_3/AlCl_3$, $AlR_2Cl/AlRCl_2$, where R=alkyl, aryl, alkenyl, alkynyl and so on are used. Additives such as but not limited to phosphoranes and amines may also be used. Without being bound by any particular theory, it is thought that by adding MAO, the cocatalyst activates the organometallic compound by generating a free coordination center.

For the heterogeneous catalyzed reaction the homogeneous activated complex is heterogenized on support material such as but not limited to silica gels, MgO, $Al_2O_3$, and such. Therefore the catalyst is stirred together with the support for 20 minutes in a suitable solvent (for example, toluene) and can be used in a fixed bed reactor after removing the solvent.

Example 2

Preparation of the Ligand (Equation (3) Below):

To a solution of 1.5 g (7 mmol) of p-iodo-aniline and 0.5 g (3 mmol) of 2,6-diacetylpyridine in 25 ml of toluene, 0.5 g of silica-alumina catalyst and 5 g molecular sieve were added and stirred for 24 hours at 50° C. The cold solution was filtered over sodiumsulfate and washed several times with toluene. The solvent was removed in vacuo.

(3)

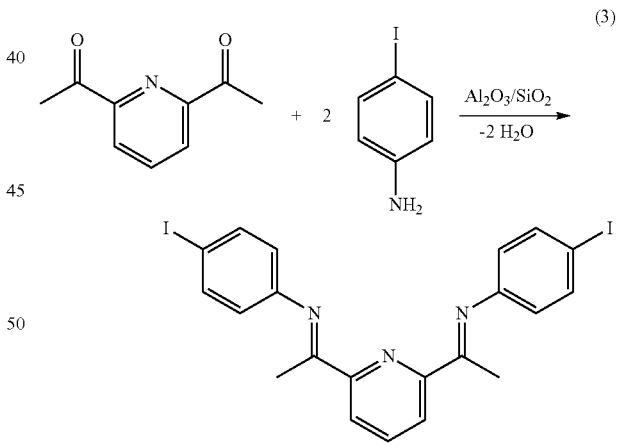

Preparation of the Complex:

To 0.2 g (0.4 mmol) of p-iodo-bis(imino)pyridine in 30 ml of n-butanole, 57 mg (0.4 mol) of $FeCl_3$ were added and stirred for two hours at room temperature and filtered. The precipitate was washed with pentane and dried in vacuo.

Preparation of the Catalyst:

10 mg of di-iodo-bis(imino)pyridine-Fe(III) complex was mixed with 4.2 ml MAO (10% in toluene, Fe:Al=1:500), 20 ml of 1-hexene were added and the mixture stirred for five hours at 4° C.

Without being bound by any particular theory, the dimerization of alpha-hexene may occur as illustrated in equation (4) below:

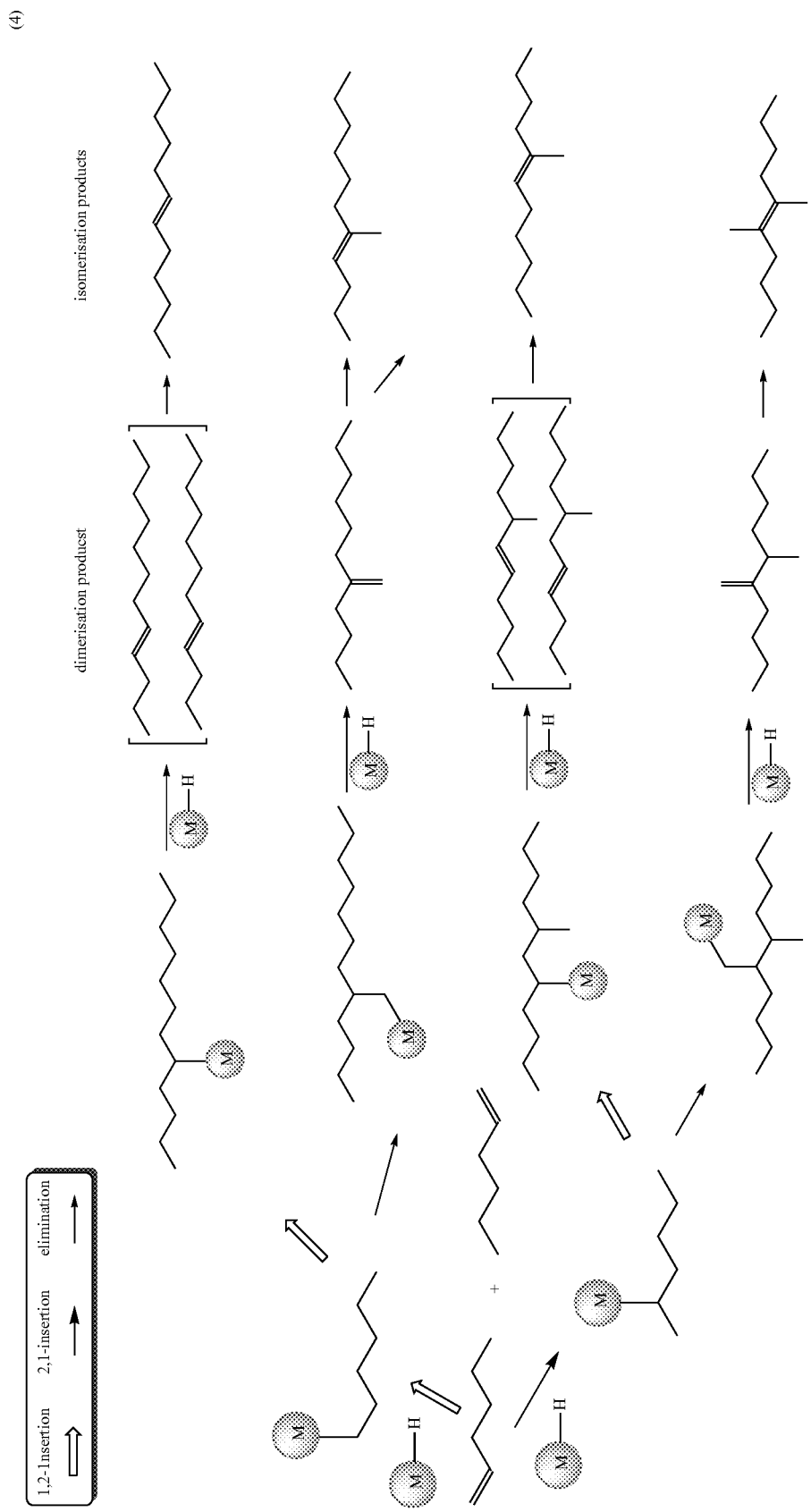

The reaction products depend on 1,2- or 2,1-insertion and are able to isomerize. FIG. 1 illustrates a GC spectra of the reaction products after five hours. From 29.9-33.2 min dodecenes are detected, octadecenes are detected from 34.0-34.8 min and higher oligomers are detected after 36 minutes. Not shown, but available on request, are additional data for hexene dimerization.

In some embodiments of the invention, the organometallic catalyst is immobilized on one or more supports selected from the group consisting of silica, zeolite and partially hydrolyzed trimethylaluminum ("PHT").

Example 3

General Synthesis Procedure for the Silicagel/PHT Catalyst System:

At room temperature, 30 ml of a 2.0M trimethylaluminum solution in toluene were added to a suspension of 2.0 g calcined silica gel in 100 ml toluene. 0.75 ml water was bubbled through the suspension as a moist argon flow. Thereupon, the reaction mixture heated itself to 60° C. After 10 min, the suspension became suddenly highly viscous. After cooling to room temperature, the mixture was stirred vigorously for 2 hours. 0.23 mmol of the catalyst precursor were added as solids and stirred for 5 min. Then the mixture was filtered and the solution dried in vacuo. The filtrate was colorless and contained no organic or inorganic components besides the solvent. Yields of the catalyst: 5.40 g (>95% calculated on aluminum content) of a powder colored according to the catalyst precursor.

Example 4

General Synthesis Procedure for the Prepolymerized Silica Gel/PHT Catalyst System:

The synthesis was analogous to Example 3. However, an ethylene pressure of 1.0 bar was applied for 15 min at 25° C. prior to the filtration of the catalyst suspension. The reaction vessel was saturated with hydrogen at ambient pressure prior to the addition of ethylene. During prepolymerization, the color of the reaction mixture changed to dark-brown and it became highly viscous. After filtration and drying in vacuo, 5.60 g of a slightly colored powder were obtained. The polyethylene portion of the catalyst was obtained from the difference between the weight before and after prepolymerization.

What is claimed is:

1. A process for the dimerization of olefins comprising the steps of:
    modifying a support material containing —OH groups with an alkylaluminum compound to form a modified support material;
    mixing an ionic liquid having a melting point below about 100° C. with a buffer to form a buffered ionic liquid;
    mixing the buffered ionic liquid with an organometallic complex of the formula

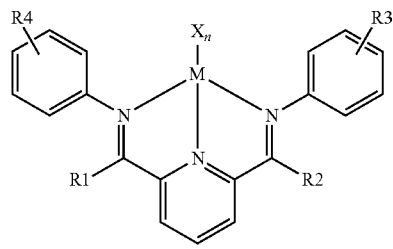

where X is a halogen, n=2 or 3, M=Ti, V, Cr, Mn, Co and Ni and R1, R2, R3 and R4 are selected from the group consisting of hydrogen, alkyl, aryl, alkenyl, alkynyl, alkyloxy, substituted aryl, and X to form a buffered ionic liquid/catalyst complex;
    mixing the buffered ionic liquid/catalyst complex with the modified support material to form an immobilized buffered catalyst; and
    mixing the immobilized buffered catalyst with one or more alpha-olefins.

2. The process of claim 1 wherein M=Ti, V, Cr, Mn and Ni, X=Cl, n=3 and R1, R2, R3 and R4=hydrogen.

3. The process of claim 1 wherein the one or more alpha-olefins is selected from the group alkenes having between three and ten carbon atoms.

4. The process of claim 1 wherein the ionic liquid comprises a salt selected from the group consisting of $AlCl_3$, $AlRCl_2$ and $AlR_2Cl$, where R is an alkyl chain.

5. The process of claim 1 wherein the ionic liquid comprises a cation selection from the group consisting of ammonium, imidazolium, sulfonium and phosphonium salts.

6. The process of claim 1 wherein the alkylaluminum compound is chloroethylaluminum.

7. The process of claim 1 wherein the support is silica, zeolite, partially hydrolyzed trimethylaluminum, or a mixture thereof.

8. The process of claim 1 wherein the step of mixing the immobilized buffered catalyst with one or more alpha-olefins is conducted in a fixed bed reactor.

9. The process of claim 1 wherein the alpha-olefin dimerization reaction comprises 1,2- or 2,1-insertion.

10. The process of claim 1 further comprising drying the immobilized buffered catalyst to form a powder prior to the mixing the immobilized buffered catalyst with one or more alpha-olefins.

* * * * *